US007169602B2

(12) United States Patent
Sandell

(10) Patent No.: US 7,169,602 B2
(45) Date of Patent: Jan. 30, 2007

(54) SAMPLE SUBSTRATE FOR USE IN BIOLOGICAL TESTING AND METHOD FOR FILLING A SAMPLE SUBSTRATE

(75) Inventor: Donald R. Sandell, San Jose, CA (US)

(73) Assignee: Applera Corporation, Foster City, CA (US)

( * ) Notice: Subject to any disclaimer, the term of this patent is extended or adjusted under 35 U.S.C. 154(b) by 649 days.

(21) Appl. No.: 10/309,311

(22) Filed: Dec. 4, 2002

(65) Prior Publication Data

US 2004/0110275 A1 Jun. 10, 2004

(51) Int. Cl.
*C12M 1/34* (2006.01)

(52) U.S. Cl. ............................... 435/288.4; 435/288.5; 435/305.3; 422/102; 422/103; 422/942; 220/23.2; 220/23.8; 220/523; 220/524; 206/561; 206/533; 137/832

(58) Field of Classification Search ............ 435/305.3; 206/561; 422/942; 220/524, 23.2, 23.8
See application file for complete search history.

(56) References Cited

U.S. PATENT DOCUMENTS 3,483,997 A * 12/1969 Ritter .......................... 211/76
3,760,973 A * 9/1973 Canning et al. ........... 220/23.8
4,253,572 A * 3/1981 Halbich ...................... 206/538
4,431,307 A * 2/1984 Suovaniemi ................ 356/246
4,593,819 A 6/1986 Will
4,721,679 A 1/1988 Yiu et al.
5,038,852 A 8/1991 Johnson et al.
5,333,675 A 8/1994 Mullis et al.
5,342,581 A 8/1994 Sanadi
5,346,672 A 9/1994 Stapleton et al.
5,443,890 A 8/1995 Ohman
5,484,734 A 1/1996 Kimura
5,487,872 A 1/1996 Hafeman et al.
5,593,130 A 1/1997 Hansson et al.
5,632,399 A 5/1997 Palmieri et al.
5,683,659 A 11/1997 Hovatter
5,722,553 A 3/1998 Hovatter
5,749,730 A 5/1998 Johnsen et al.
5,863,791 A 1/1999 Baldszun et al.
5,928,907 A 7/1999 Woudenberg et al.
6,000,535 A 12/1999 Berk et al.
6,005,183 A 12/1999 Akai et al.
6,015,674 A 1/2000 Woudenberg et al.
6,027,694 A 2/2000 Boulton et al.
6,042,789 A 3/2000 Antonenko et al.
6,161,696 A 12/2000 Lashley (Continued)

FOREIGN PATENT DOCUMENTS

DE 196 10 146 C1 6/1997

(Continued)

OTHER PUBLICATIONS

PCT International Search Report for International application No. PCT/US03/38561 mailed Apr. 27, 2004.

*Primary Examiner*—William H. Beisner

(57) ABSTRACT

A sample substrate for use in biological testing is provided having a first member defining at least one sample well and a second member including at least one sample well closure element. The at least one sample well closure element may be configured to substantially seal a corresponding sample well. Methods of filling the sample substrate are also provided.

17 Claims, 8 Drawing Sheets

CLOSE

U.S. PATENT DOCUMENTS

| | | | |
|---|---|---|---|
| 6,190,619 | B1 | 2/2001 | Kilcoin et al. |
| 6,193,088 | B1 | 2/2001 | Vincent et al. |
| 6,229,603 | B1 | 5/2001 | Coassin et al. |
| 6,261,523 | B1 | 7/2001 | Schembri |
| 6,272,939 | B1 | 8/2001 | Frye et al. |
| 6,340,589 | B1 | 1/2002 | Turner et al. |
| 6,383,820 | B1 | 5/2002 | Bunn et al. |
| 6,436,350 | B1 | 8/2002 | Stanchfield et al. |
| 2002/0001848 | A1 | 1/2002 | Bedingham et al. |
| 2002/0028507 | A1 | 3/2002 | Heimberg et al. |
| 2002/0047003 | A1 | 4/2002 | Bedingham et al. |
| 2002/0048533 | A1 | 4/2002 | Harms et al. |
| 2002/0064885 | A1 | 5/2002 | Bedingham et al. |
| 2002/0092767 | A1 | 7/2002 | Bjornson et al. |

FOREIGN PATENT DOCUMENTS

| | | | |
|---|---|---|---|
| EP | 0 754 496 | | 1/1997 |
| EP | 0 606534 | B1 | 12/1997 |
| WO | WO 86/07288 | | 12/1986 |
| WO | WO 01/15807 | A1 | 3/2001 |
| WO | WO 01/28684 | A2 | 4/2001 |
| WO | WO 02/00347 | | 1/2002 |
| WO | WO 02/01180 | A2 | 1/2002 |
| WO | WO 02/01181 | A2 | 1/2002 |

* cited by examiner

SPOT

CLOSE

FILL

SEAL

SAMPLE SUBSTRATE FOR USE IN BIOLOGICAL TESTING AND METHOD FOR FILLING A SAMPLE SUBSTRATE

FIELD

The present teachings relate to devices for storing samples to be tested. More particularly, the present teachings relate to various sample substrates for use in biological testing devices, and methods for filling a sample substrate.

BACKGROUND

Biological testing has become an important tool in detecting and monitoring diseases. In the biological testing field, thermal cycling is used to amplify nucleic acids by, for example, performing polymerase chain reaction (PCR) and other reactions. PCR may be carried out using "consumables", which are sample substrates that are relatively inexpensive, disposable, readily available, and often having multiple sample wells, for example, such as PCR tubes, chips, sample plates, trays, or microcards, thus, enabling varying volumes of samples to be processed and tested. As mentioned above, one such consumable that may enable a number of reactions in a relatively small amount of space is commonly known as the microcard, a spatial variant of the micro-titer plate, which may contain individual wells with a wide range of volumes.

Microcards may be "pre-loaded" with a dried reagent or other similar element of a sample to be tested in each of the sample wells. This pre-loading may be done by the microcard manufacturer who provides the pre-loaded card to the testing facility to be further loaded with a desired test sample. Such a pre-loaded microcard may limit the capabilities of a testing facility to configure their card for a desired test to the configuration of cards they have already ordered from the manufacturer. In addition, the testing facility may be required to wait for a newly configured card to be delivered by the manufacturer, possibly delaying desired testing. Microcards in use today may be filled at the testing facility using filling devices that may be costly for smaller testing facilities to maintain. There exists a need for a low-cost consumable that may be fully configured with varying test samples by a user to a desired configuration for testing.

SUMMARY

In accordance with the teachings, a sample substrate for use in biological testing is provided having a first member defining at least one sample well and a second member including means for substantially sealing the at least one sample well. The means for substantially sealing may be movable with respect to a remainder of the second member.

As used herein, the term "substantially seal" refers to a state whereby a sample well is essentially closed off so that material contained within the sample well remains within the sample well, and material outside of the sample well is substantially inhibited from flowing into the sample well. "Substantially sealed" is not intended to define a state whereby no material can get in or out of the sample well, but just a state of sealing sufficient to allow a level of isolation of a sample within the sample well for desired testing to occur. By way of example only, this state of being "substantially sealed" is intended to describe a state similar to that achieved by staking, a method of sealing sample wells within a microcard by deforming a metal backing of a microcard to sufficiently isolate the sample to allow testing to occur.

According to another aspect, a sample substrate for use in biological testing may comprise a first member defining a plurality of sample wells for containing a sample to be tested and a second member including a plurality of sample well closure elements. Each sample well closure element may be movable with respect to a remainder of the second member. The second member may be movable with respect to the first member from an uncovered position, wherein the plurality of sample wells is uncovered, to a covered position, wherein the plurality of sample wells is substantially covered by the second member. At least one of the plurality of sample well closure elements may be configured to substantially seal a corresponding sample well when the second plate is in the covered position, by moving the at least one of the plurality of closure elements from a first predetermined position to a second predetermined position.

According to yet another aspect, at least one of the plurality of closure elements may comprise a cap and an annular rim surrounding the cap.

In another aspect, the cap may include a cylindrical portion configured to engage an inner surface of its corresponding sample well.

In a further aspect, the annular rim may comprise a snap-action hinge that moves the cap from the first predetermined position to the second predetermined position upon a sufficient force being imparted on the cap.

In yet another aspect, the annular rim may be configured to allow the at least one of the plurality of caps to move with respect to the remainder of the second member from the first predetermined position to the second predetermined position.

According to another aspect, a portion of the at least one of the plurality of closure elements may reside within the corresponding sample well when the closure element is in the second predetermined position.

In another aspect, at least one of the at least one of the plurality of closure elements and its corresponding sample well may comprise a flexible portion configured to deflect to maintain substantially the same volume of the sample to be tested within the sample well when the at least one of the plurality of closure elements is in the second predetermined position as compared to a volume of the sample to be tested when the closure element is in the first predetermined position.

In yet another aspect, the sample substrate may include at least one reservoir in fluid communication with the at least one of the plurality of sample wells.

According to another aspect, the reservoir may be in fluid communication with the at least one of the plurality of sample wells via a fluid channel.

In further aspect, the sample substrate may comprise a branch fluid channel between the fluid channel and the at least one of the plurality of sample wells.

According to yet another aspect, the at least one of the plurality of closure elements may permit fluid communication between its corresponding sample well and the reservoir when in the first predetermined position and prevents fluid communication between the reservoir and the sample well when in the second predetermined position.

According to another aspect, at least one reservoir may be capable of being filled with the sample to be tested when the second member is in the covered position.

In another aspect, the at least one reservoir may comprise a plurality of reservoirs.

In yet another aspect, each of the plurality of reservoirs may be in fluid communication with a separate portion of the plurality of sample wells.

In another aspect, at least a portion of the at least one closure element may comprise a light pipe.

In another aspect, a light pipe may be located on the flexible portion of the at least one closure element.

According to another aspect, the plurality of sample wells may be positioned in a matrix.

According to yet another aspect, the plurality of closure elements may be positioned in a matrix and each of the plurality of closure elements may be configured to mate with a corresponding one of the plurality of sample wells.

In another aspect, the sample substrate may comprise at least one of 4, 8, 12, 16, 24, 48, 96, 128, 384, and 1536 sample wells and corresponding closure elements.

In yet another aspect, an adhesive membrane may be positioned between the first and second member when the microcard is in the covered position.

According to another aspect, the adhesive membrane, before a first use of the microcard, may affixed to the first member or the second member.

According to yet another aspect, the first member may comprise a first plate and the second member may comprise a second plate.

In another aspect, the sample substrate comprises a microcard. In yet another aspect, the sample substrate comprises a micro-titer plate.

In another aspect, a method of filling a sample substrate may comprise placing a first material into at least one of a plurality of sample wells defined by a first member of the sample substrate, placing a second material into at least one of the plurality of sample wells, moving a second member of the sample substrate with respect to the first member to substantially cover the plurality of sample wells, and moving at least one of a plurality of closure elements comprised by the second member from a first predetermined position to a second predetermined position to substantially seal the at least one of the plurality of sample wells.

In yet another aspect, the first material may comprise a reagent and the second material may comprise a biological sample to be tested.

According to another aspect, the first material and the second material may be placed into the at least one of the plurality of sample wells before the second plate is moved to substantially cover the plurality of sample wells.

According to a further aspect, the first and second materials may be placed into the at least one of the plurality of sample wells via a pipette.

According to yet another aspect, the first material may be placed into the at least one sample well before the second member is moved to substantially cover the plurality of sample wells.

In another aspect, the first material may be placed into the at least one sample well via a pipette.

In yet another aspect, the second material may be placed into the at least one of the plurality of sample wells after the second member is moved to substantially cover the plurality of sample wells.

According to another aspect, the second material may be placed in a reservoir of the sample substrate and transferred to the plurality of sample wells by at least one of vacuum loading and centrifugal loading.

According to yet another aspect, the moving at least one of the plurality of closure elements comprises using a fixture to apply pressure to the at least one of the plurality of closure elements thus moving the at least one of the plurality of closure elements with respect to its corresponding sample well and with respect to the second member.

In another aspect, a portion of at least one of the plurality of closure elements may deform when the plurality of closure elements move to substantially seal its corresponding sample well.

In yet another aspect, a portion of at least one of the plurality of sample wells may deform when its corresponding closure element moves to substantially seal the sample wells.

According to another aspect, a portion of at least one of the closure elements may be at least partially submerged in the first and second materials contained in its corresponding sample well when the at least one closure element substantially seals its corresponding sample well.

According to yet another aspect, the submerged portion of the closure element may comprise a light pipe.

In one aspect, a sample substrate for use in biological testing may comprise a first member defining a plurality of sample wells, and a second member including a plurality of corresponding sample well closure elements, each of the plurality of closure elements corresponding to one of the plurality of sample wells. The second member may be movable with respect to the first member from an open position, wherein the plurality of sample wells are open, to a covered position, wherein the plurality of sample wells are substantially covered by the second member. The plurality of sample well closure elements may each be movable with respect to a remainder of the second member from a first predetermined position to a second predetermined position configured to substantially seal a corresponding sample well when the second member is in the closed position.

In another aspect, a sample substrate for use in biological testing may comprise a first member defining a plurality of sample wells for containing a sample to be tested and a second member including a plurality of sample well closure elements. Each sample well closure element may be movable with respect to a remainder of the second member. The second member may be movable with respect to the first member from an uncovered position, wherein the plurality of sample wells are uncovered, to a covered position, wherein the plurality of sample wells is substantially covered by the second member. At least one of the plurality of sample well closure elements may be configured to substantially seal a corresponding sample well when the second plate is in the covered position, by moving the at least one of the plurality of closure elements from a first predetermined position to a second predetermined position. The microcard, before a first use, may have sample wells containing no material to be tested and may be in the uncovered position.

According to another aspect, a sample substrate for use in biological testing may comprise a first member defining a plurality of sample wells for containing a sample to be tested and a second member including a plurality of sample well closure elements. Each sample well closure element may be movable with respect to a remainder of the second member. The second member may be movable with respect to the first member from an uncovered position, wherein the plurality of sample wells is uncovered, to a covered position, wherein the plurality of sample wells is substantially covered by the second member. At least one of the plurality of sample well closure elements may be configured to substantially seal a corresponding sample well when the second plate is in the covered position, by moving the at least one of the plurality of closure elements from a first predetermined position to a second predetermined position. The microcard may be in the covered position and may have material to be tested contained within at least one of the sample wells, the at least one of the plurality of sample wells being substantially sealed by the closure element.

In yet another aspect, a sample substrate for use in biological testing may comprise a first member defining a plurality of sample wells for containing sample to be tested and a second member including a plurality of sample well closure elements and a surface connecting the sample well closure elements. Each sample well closure element may include a cap with a projecting member dimensioned to fit into a corresponding sample well and a flexible annular hinge member connecting the cap and the surface of the second member. The flexible annular hinge member may be configured to snap between a first discrete position in which the cap substantially covers the corresponding sample well and a second discrete position in which the cap substantially seals the corresponding sample well.

In still another aspect, a sample substrate for use in biological testing may comprise a first plate-like member defining an array of sample wells for containing sample to be tested and a second plate-like member including an array of sample well closure elements and a surface connecting the sample well closure elements. The sample well closure elements may be positioned to correspond with the array of sample wells. Each sample well closure element may including a cap with a cylindrical member dimensioned to fit into a corresponding sample well and a bottom portion, and a flexible annular hinge member connecting the cap and the surface of the second plate-like member. The flexible annular hinge member may include an over-center hinge so that the hinge member snaps between a first discrete position in which the cap is spaced from the sample well, and a second discrete position in which the bottom portion of the cap is positioned within the sample well to substantially seal the corresponding sample well.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate at least one exemplary embodiment. In the drawings.

DESCRIPTION OF VARIOUS EMBODIMENTS

Figure 1:
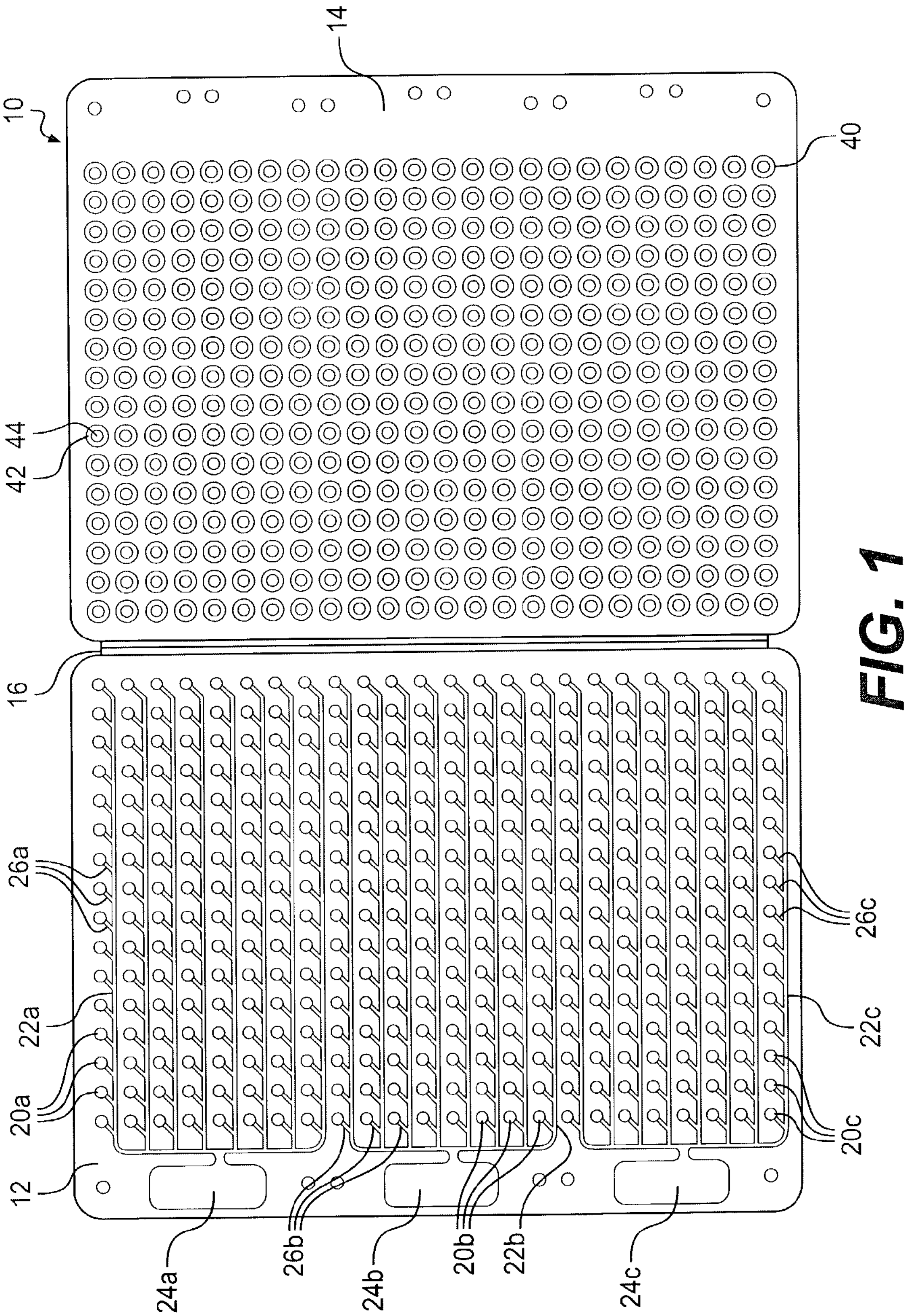
FIG. 1 is a plan view of a microcard having 384 samples wells in an open position.

Reference will now be made to various exemplary embodiments, examples of which are illustrated in the accompanying drawings. Wherever possible, the same reference numbers are used in the drawings and the description to refer to the same or like parts, and the same reference numbers with alphabetical suffixes or numerical prefixes are used to refer to similar parts.

In accordance with various embodiments, a sample substrate is provided. In one aspect, the sample substrate may be filled with one or more samples to be tested in a testing device. Such a testing device may include a thermal cycler or other suitable biological testing device. In various aspects, the sample substrate may comprise a plurality of sample wells located in a first member, with each of the sample wells having an associated closure element located in a second member. In some embodiments, the two members may be formed of a single piece and movable with respect to one another to allow open access to the sample wells in a first ("uncovered") position and to cover the sample wells in a second ("covered") position.

Figure 2:
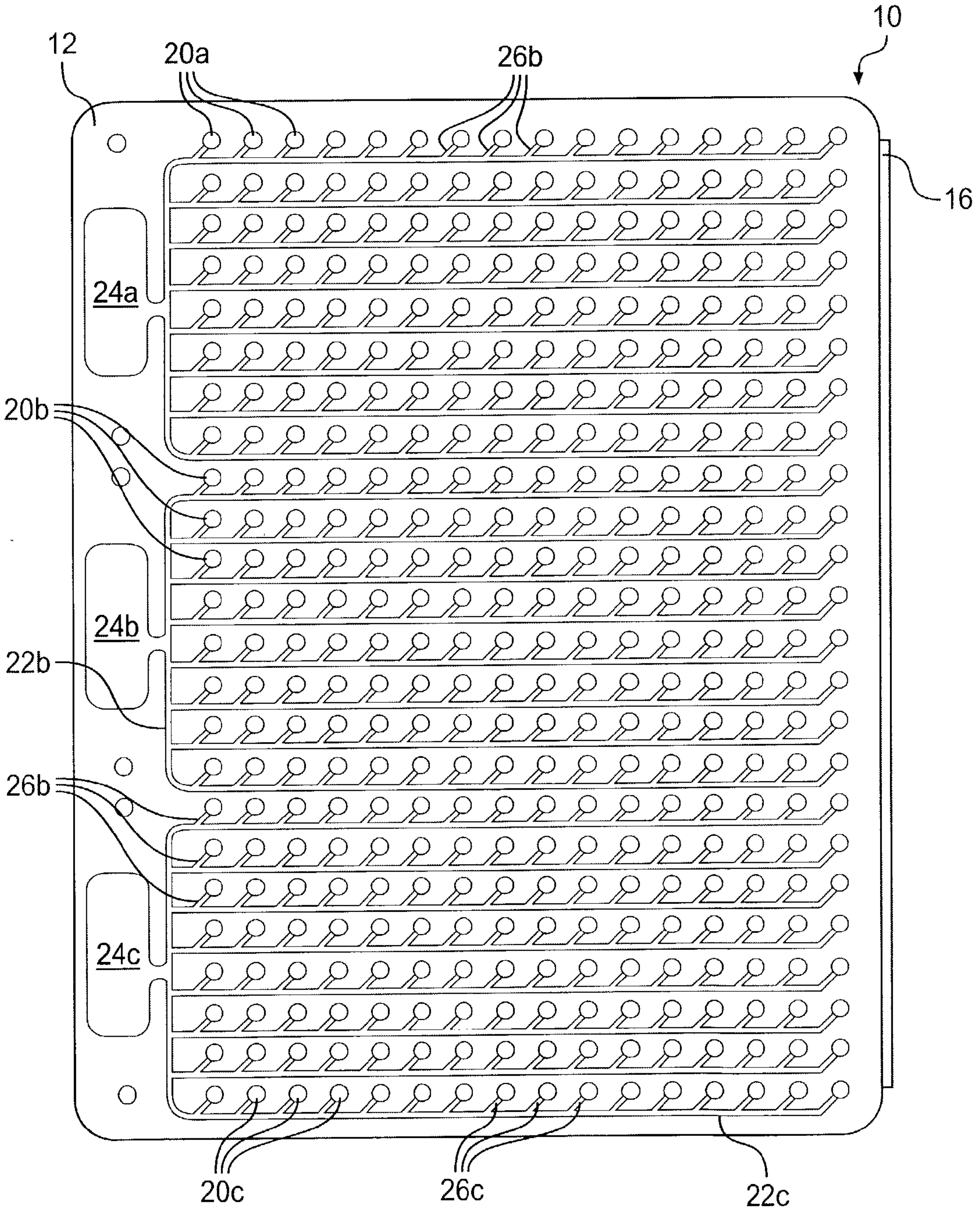
FIG. 2 is a plan view of the microcard of FIG. 1 in a closed position.

It should be understood that although the term "microcard" is used in the specification, the present teachings are suitable in any type of sample substrate such as, for example, micro-titer plates, sample trays, etc. In various embodiments, such as shown in FIGS. 1–3, a sample substrate such as microcard 10 is provided. Microcard 10 may be configured for thermally cycling samples of biological material in a thermal cycling device. The thermal cycling device may be configured to perform nucleic acid amplification on samples of biological material. One method of performing nucleic acid amplification of biological samples is PCR. Various PCR methods are known in the art, as described in, for example, U.S. Pat. Nos. 5,928,907 and 6,015,674 to Woudenberg et al., the complete disclosures of which are hereby incorporated by reference for any purpose. Other methods of nucleic acid amplification include, for example, ligase chain reaction, oligonucleotide ligations assay, and hybridization assay. These and other methods are described in greater detail in U.S. Pat. Nos. 5,928,907 and 6,015,674, which are also incorporated herein by reference.

In certain embodiments, the microcard may be used with a real-time detection system. Real-time detection systems are known in the art, as also described in greater detail in, for example, U.S. Pat. Nos. 5,928,907 and 6,015,674 to Woudenberg et al., incorporated herein above. During real-time detection, various characteristics of the samples are detected during the thermal cycling. Real-time detection permits accurate and efficient detection and monitoring of the samples during the nucleic acid amplification. Alternatively, the microcard may be used in a thermal cycling device that performs endpoint detection of the nucleic acid of the samples. Additional examples of thermal cyclers used in PCR reactions include those described in U.S. Pat. Nos. 5,038,852 and 5,333,675, the contents of both of which are hereby incorporated by reference herein.

In FIG. 1, a plan view of a microcard 10 is shown in an open position and having a first member, or plate, 12 and a second member, or plate, 14. First plate 12 and second plate 14 are connected via a hinge element 16, which may be of the living hinge type, for example. Microcard 10 may be made formed as a single unit out of a material such as polypropylene that is both suitable for PCR testing and for comprising a living hinge. Other materials may also be used that are capable of providing the proper characteristics suitable for use in a PCR testing device. Although in certain embodiments it may be desirable for microcard 10 to be formed as a single piece it may also be possible to form plates 12 and 14 as separate pieces joined by a hinge element that may be integral with one of plates 12 or 14 and attached to the other or a separate element attached to both.

As shown in FIG. 1, plate 12 defines a plurality of sample wells (or sample chambers) 20*a*–20*c*. As embodied herein, plate 12 defines 384 sample wells divided into three sets of 128 sample wells. As shown in FIG. 1, each set of 128 wells is configured in a 8×16 matrix. It should be understood that a wide variety of configurations are possible. Other common configurations include, for example, 48, 96, and 384 sample well matrices, although the present teachings are suitable with any number of sample wells. Plate 12 also defines a plurality of channels 22*a*–22*c* that connect sample wells 20*a*–20*c* via branch channels 26*a*–26*c* so as to be in fluid communication with a respective reservoir 24*a*–24*c*. Although three reservoirs 24*a*–24*c* are depicted, each in fluid communication with one-third of the 384 sample wells, other configurations are possible. For example, one reservoir may be provided that is in fluid communication with all of the sample wells 20 or there may be twenty-four reservoirs, each in communication with one of the channels. Further, any other number of reservoirs may be contemplated so as to be in communication with a desired portion of sample wells.

A sample substrate such as a microcard may be "spotted" with a reagent in one or more of the sample wells, which is then dried. As used herein, spotting defines the process of placing a fluid, for example a reagent, into a sample well, often using a pipette, but other suitable filling means may be employed. These pre-loaded microcards may then be filled with another fluid, for example a biological sample to be tested, so as to create a reaction between the reagent and the sample during the PCR process. Similar to microcard 10, traditional microcards may have one or more reservoirs that may be filled with the sample to be tested. The sample fluid contained in the reservoirs may then pass to the sample wells, for example, by vacuum loading or by centrifugal loading, whereby the card is spun in a centrifuge to transfer the liquid from the reservoir to the sample wells with which the reservoir communicates, as well as any other means known in the art for loading the sample wells with a biological sample.

Microcard 10 may be used in a somewhat similar fashion, but because it allows a user open access to each individual well, it may provide more flexibility in how the microcard is configured. For example, a user may spot a reagent of his or her choice into one or more of the sample wells 20*a*–20*c* when the microcard is in the open or "uncovered" position shown in FIG. 1. Microcard 10 may be configured so as to be compatible with automatic pipetting equipment or it may be suited for manual pipetting or other spotting means. Such a user configurable card may allow the user to decide at the time of testing what samples and reagents to use in the testing rather than relying on pre-loaded cards.

The user may also introduce a variety of reagents into the sample wells. As depicted in FIG. 1, for example, a user may introduce 128 separate reagents into each of sample wells 20*a* when the microcard is in the uncovered position. Reservoir 24*a* could then be filled with a biological sample that could react with each of the different reagents during PCR testing. This procedure could be repeated for loading reagents into sample wells 20*b*, 20*c* and a separate biological sample could be placed in each of reservoirs 24*b* and 24*c*. Such a configuration could then be used, for example, to screen three individuals for a variety of diseases or other conditions. In addition, by spotting each of wells 20*a*–20*c* with different reagents, a single biological sample could be loaded into each of reservoirs 24*a*–24*c*. Thus, with the microcard depicted in FIGS. 1–3, a single sample could be screened for 384 different properties.

In another testing configuration, each well could be loaded with a separate biological sample and one or more of the reservoirs could be loaded with a single reagent or separate reagents. This configuration, which may be referred to as a reverse card, could allow for screening of a single condition in a variety of biological samples. For example, a population could be screened for the existence of one condition. The various configurations of loading microcards described herein are merely exemplary. Other configurations both of reservoir number and sample/reagent loading in the sample wells may be apparent from the teachings of the disclosure contained herein.

Once the reservoirs 24*a*–24*c* have been filled and the sample wells 20*a*–20*c* have been appropriately spotted, plate 14 may then be folded over onto plate 12 as seen in FIG. 2, which is shown at an outside surface of plate 12. FIG. 2 shows a covered position wherein the plurality of sample wells 20*a*–20*c* are substantially covered by plate 14. Although reservoirs 24*a*–24*c* are depicted as being fully covered by plate 14, it is possible in certain embodiments for reservoirs 24*a*–24*c* to be provided with an opening (not shown) so that reservoirs 24*a*–24*c* may be filled after plate 14 is moved into position over plate 12. The opening may be in the form of a through hole located in either of plate 12 or plate 14 so as to allow access by a pipette or other filling means, or as is possible with centrifugally loaded microcards, the reservoir may be open substantially along an edge at the periphery of the card.

With traditional microcards, the sample wells are often provided in a polypropylene card, although, other PCR compatible materials besides polypropylene may be used. A foil backing may be adhered to the card to close off each of the sample wells, channels, and/or reservoirs thus maintaining the desired separation between various of the reservoirs, sample wells, and reservoirs. In order to provide a similar isolated covering, an adhesive membrane 30 (see FIGS. 3A–3D) may be provided between plates 12 and 14. Adhesive membrane 30 may be made of a material such as polypropylene, LEXAN, MYLAR, or any other suitable PCR-compatible material. Adhesive membrane 30 may be initially affixed to either of plates 12 or 14 with an adhesive backing to provide the desired seal between plates 12 and 14 once microcard 10 is in the closed position. As depicted in FIGS. 3A–3D, membrane 30 is initially affixed to plate 14 and moves into contact to adhere with plate 12. Membrane 30 is preferably configured to adhere to plate 12 so that fluid communication between reservoirs 24*a*–24*c* and sample wells 20*a*–20*c* via channels 22*a*–22*c* and branch channels 26*a*–26*c* is maintained when plates 12 and 14 are adhered together. Membrane 30 may be coated with a PCR-compatible adhesive, such as one that is non-fluorescing and has high-tack properties. It is desirable that membrane 30 be configured so as not to inhibit fluid flow from reservoirs 24*a*–24*c* to each of the sample wells 20*a*–20*c*.

Figure 3A:
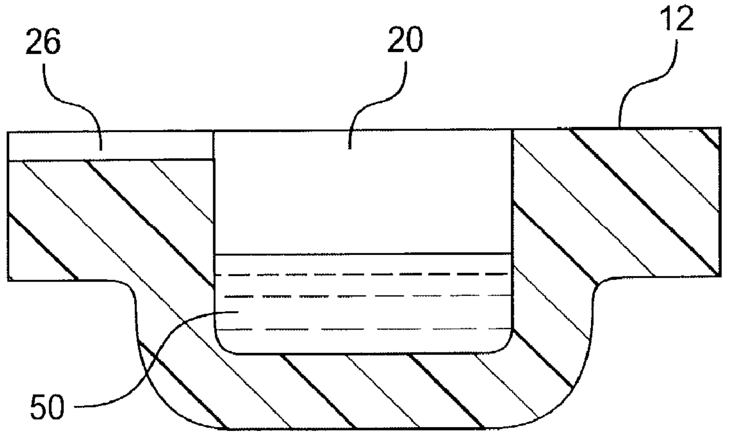
FIGS. 3A–3D are partial section views of a sample well of the microcard of FIG. 1 showing a progression of steps to fill and substantially seal the sample wells.
Figure 3B:
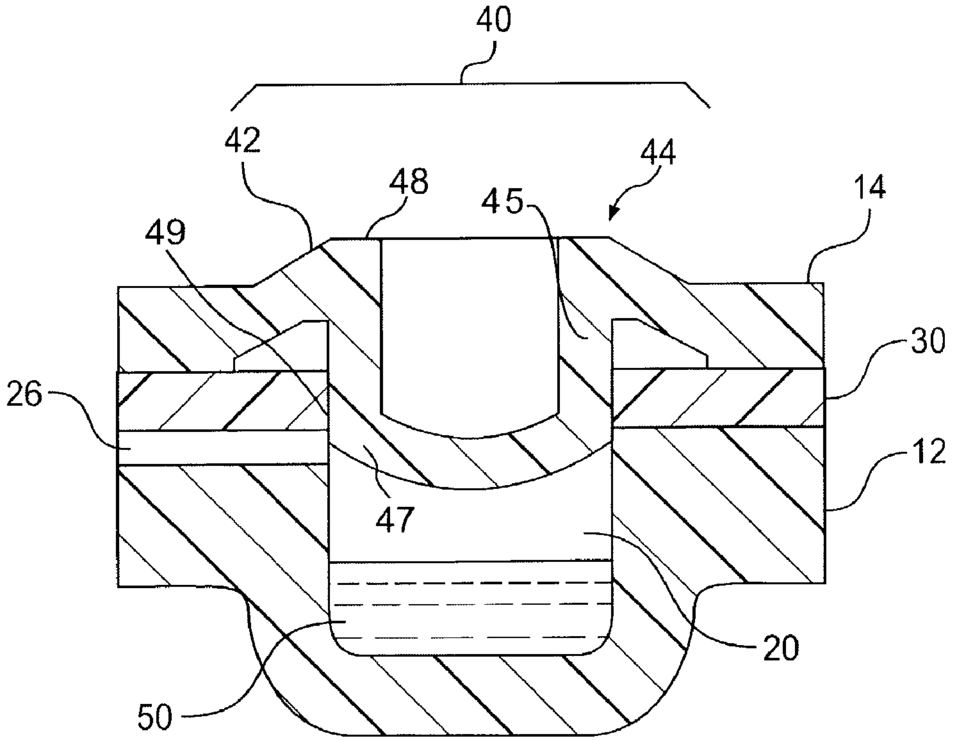

Plate 14, which may be moved into position over plate 12, comprises a plurality of closure elements 40, as shown, for example, in FIG. 3B. Each closure element 40 is configured to be positioned relative to a corresponding sample well 20 so as to substantially cover and then substantially seal the sample well once it has been filled with the desired fluids for reaction during PCR testing. In various embodiments, the closure element 40 comprises a flexible annular rim 42 and a cap 44. In the embodiment shown in FIG. 3B, the flexible annular rim 42 defines a hinge that connects plate 14 to cap 44. The flexible annular rim 42 surrounds cap 44, but permits axial movement of cap 44 during a closing procedure described below.

Figure 3C:
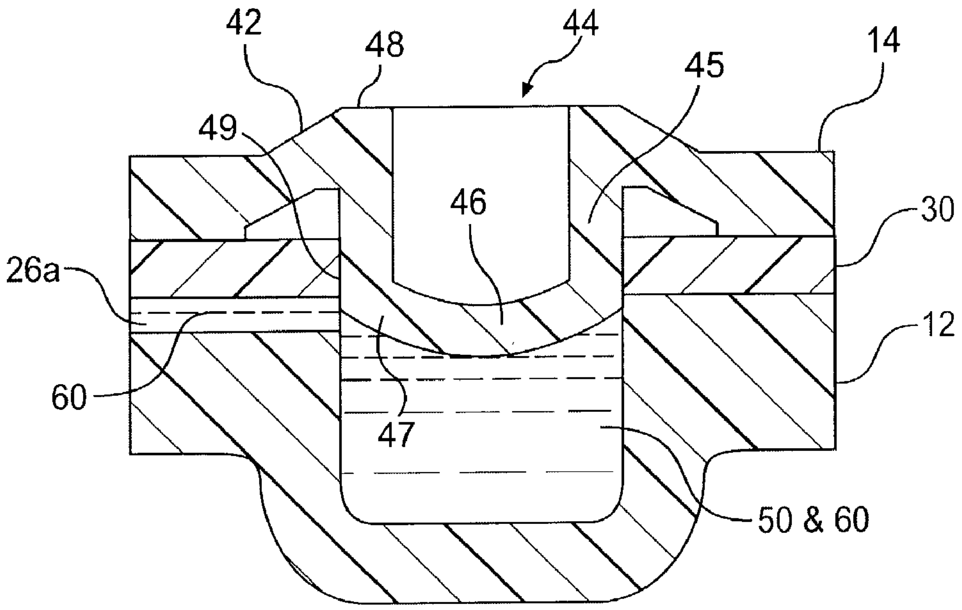
Figure 3D:
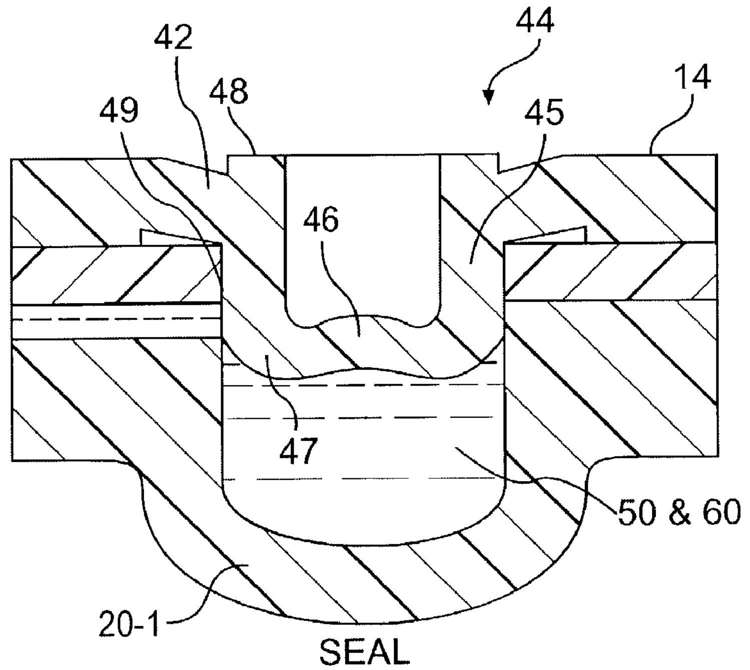

In various embodiments, cap 44 comprises a cylindrical member 45 and a bottom member 47. The cylindrical member 45 extends downward from a top surface 48 of the cap 44. The cylindrical member 45 includes an outer surface 49 preferably dimensioned to closely fit or have an interference fit with the inner cylindrical surface of the sample well 20 to substantially seal the sample well when the cap is moved downward into the sample well. The cap 44 may move downward by an external force being placed on the top surface 48 of the cap, causing the annular rim (or hinge) 42 to pivot so that the cap 44 moves axially in the sample well 20. The annular rim 42 shown in FIGS. 3B–3D is configured so that it snaps downward from a first predetermined (or discrete) position (FIGS. 3B–3C) to a second predetermined (or discrete) position (FIG. 3D) downward from the first predetermined position. The annular rim 42 may define an over-center hinge that will maintain the cap in either of two predetermined (or discrete) positions: a first position (FIGS. 3B–3C) or a second position (FIG. 3D).

FIGS. 3A–3D show a sequential operation of spotting, closing, filling, and substantially sealing one of sample wells of microcard 10 of FIG. 1 (for simplicity, the a-c designation has been dropped in reference to elements 20, 22, 24, and 26 in FIGS. 3A–3D). As embodied in FIG. 3A, sample well 20 located in plate 12 has been spotted with a reagent 50. This may be done prior to or after placing the plate 14 on plate 12. As seen in FIG. 3B, plate 14 may then be moved into a position (also called the "covered" position) over plate 12 by, for example, rotating plate 14 about hinge element 16 and pressing on plate 14. Adhesive membrane 30 may provide a seal between plates 12 and 14, but may maintain an open fluid path via channel branch 26, which connects to channel 22 and ultimately to reservoir 24. FIG. 3B shows the closure element 40 and cap 44 in a first position. In various embodiments, the first position is a discrete predetermined position of the hinge (or annular rim) 42.

FIG. 3C shows the closure element 40 and cap 44 still in the first position. As shown in FIG. 3C, fluid 60 contained in reservoir 24*a* has flown into sample well 20 via channel branch 26 due to, for example, a vacuum or centrifugal force, thereby mixing with reagent 50 in sample well 20. Once the desired fluids and reactants have been combined in sample well 20, cap 44 may be moved into a second position within sample well 20 to substantially seal, or isolate, sample well 20 from channel branch 26, as shown in FIG. 3D. In the example shown, the cap 44 may be moved to a second position by a user pressing downward on the top surface 48 of cap 44 with a sufficient force to cause the bottom portion of the cap to slide axially into sample well 20. Alternately, any type of pressing mechanism may be used to push downward on the top surface 48 of cap 44.

The hinge (or annular rim) 42 is configured so that the closure element 40 (including cap 44) snaps from the first position (shown in FIGS. 3B–3C) to the second position (shown in FIG. 3D) upon the lowering of the cap beyond a certain predetermined point. Once the cap 44 is in the second position, the cap is sufficiently lowered so that bottom member 47 of cap 44 blocks the channel branch 26, therefore preventing fluid communication between the channel branch 26 and the sample well 20. The outer surface 49 of the cylindrical member 45 of cap 44 may be configured to have a close clearance with an inner surface of the sample well 20. The engagement of the outer surface 49 of cap 44 with the inner surface of the sample well promotes substantial sealing between cap 44 and sample well 20. Caps 44, for example, could be moved into the substantially sealed position individually or substantially all at once.

In certain embodiments, the bottom member 47 of the cap may be provided with a flexible portion. As shown in FIG. 3D, the bottom member 47 may include a flexible portion 46. Likewise, as also shown in FIG. 3D, the portion of plate 12 defining sample well 20 may also be provided with a flexible portion 20-1. Flexible portions 46 and 20-1 compensate for the fluid, a combination of reagent 50 and sample 60, contained within sample well 20 as cap 44 is moved into position to substantially seal sample well 20 by bulging in opposite directions to maintain substantially the same fluid volume within sample well 20. As used herein, "substantially the same volume" is intended to refer to the volume of material contained in the sample well before and after cap 44 is moved into place to substantially seal sample well 20. Substantially the same volume is not intended to mean that the volume within the sample well remains exactly the same, and is intended to allow for some amount of material to possibly flow out of sample well 20 as cap 44 is moved into place. By incorporating flexible portions 46 and 20-1 into microcard 10, cap 44 and sample well 20 are capable of compensating for at least some of the sample material that would otherwise be displaced by cap 44 as it moves into place within the sample well. With a microcard of the present teachings, radiation may be directed to a detecting device either through cap 44 or through the bottom of sample well 20 depending on the configuration of the PCR testing device used.

During PCR testing, undesirable condensation may form within the sample well and obscure a viewing window into sample well 20 through which radiation, e.g., fluorescence, may pass and be detected by the PCR testing apparatus. An advantage achieved by various embodiments of a microcard according to the present teachings is that cap 44 may be inserted within sample well 20 so that a portion, for example flexible portion 46, is in contact with the sample. With a portion of cap 44 in direct contact with the sample, radiation may more easily pass through plate 14 without being affected by any potential condensation within sample well 20.

In addition, with conventional devices, it may be necessary to stake the sample wells after they have been filled with the desired reactants. In the case of a microcard with a foil backing, this is often accomplished by deforming a metal backing with a stylus or other suitable device so that the foil backing protrudes into a feed channel, such as channel branch 26, and blocks it so that it is no longer in fluid communication with its feed channel and reservoir. Closure element 40 may perform this function of substantially sealing sample well 20 through its snap-fit into well 20, thus eliminating the need to stake the microcard.

In order to move caps 44 into the substantially sealed position, a fixture may be provided that could contact the top surface 45 of caps 44 and press the caps into position within sample wells 20. This same fixture could be provided as a two-stage press that is also capable of aligning and mating plates 12 and 14 before microcard 10 is filled via a centrifugal or vacuum fill, for example. Plates 12 and 14 may fit together via an interference fit whereby one of plates 12 and 14 has a rim configured to fit around a periphery of the other of plates 12 and 14 with the interference fit being sufficient to hold the two plates together. Other snap-fit means such as snap tabs as well as any other suitable closure means may be employed to fit plates 12 and 14 together. It also may be desirable to heat one plate and cool the other plate to achieve a temporary size difference between the two plates 12, 14. Plates 12 and 14 may then be moved into a closed position and, as their temperatures equalize, a tight interference fit may be achieved. The fixture used may be configured to provide this selective temperature difference between the two plates.

As is clear from the above description, the present teachings may also include a method of filling a sample substrate.

Figure 4:
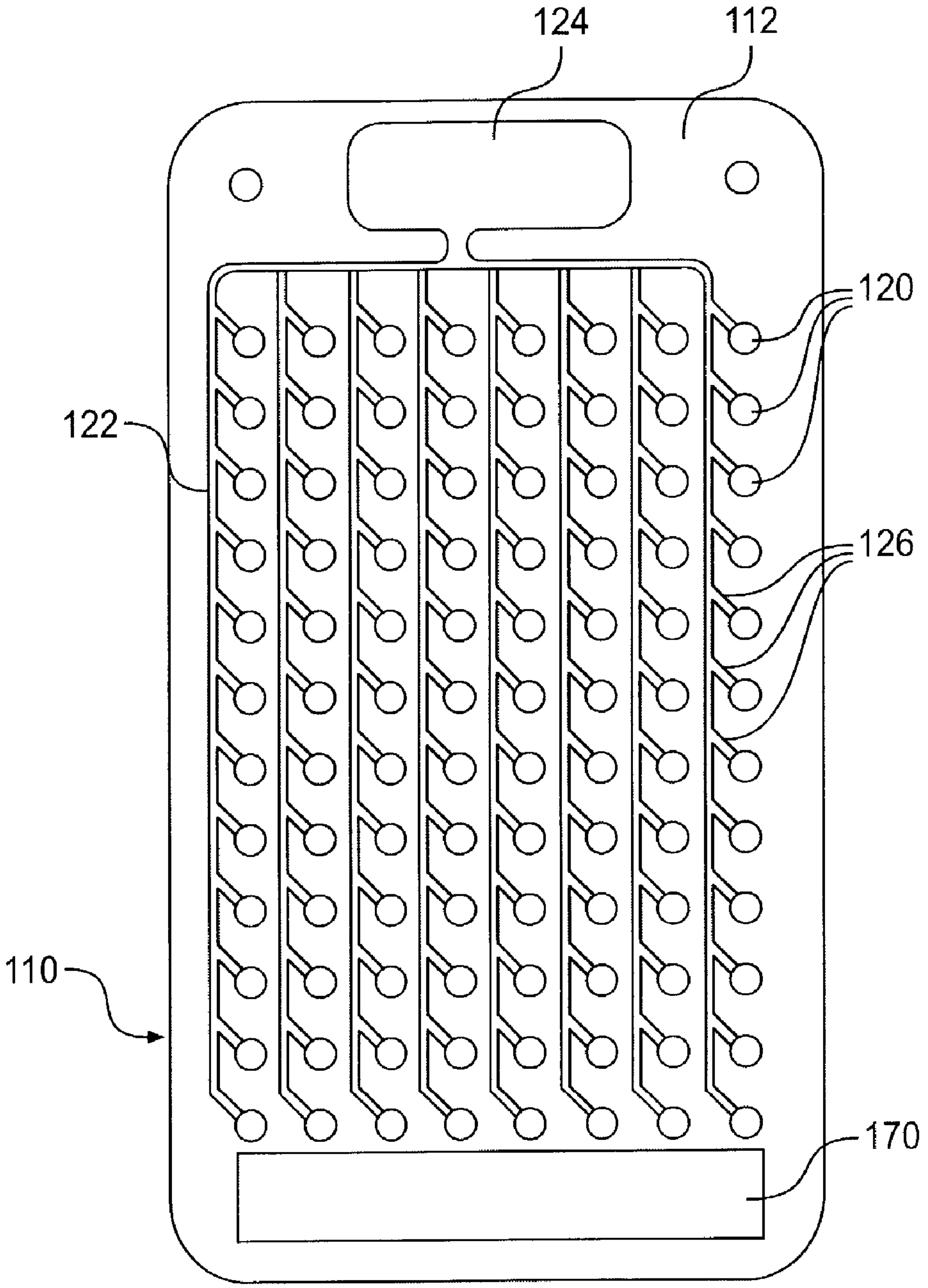
FIG. 4 is a plan view of an alternative embodiment of a microcard having 96 sample wells.

As mentioned above, the microcard may have other configurations including but not limited to the number of sample wells and reservoirs. A microcard 110 is depicted in FIG. 4 in a closed position and is viewed facing an outer surface of plate 112. Microcard 110 is similar in many respects to the microcard depicted in FIG. 1, but has 96 sample wells 120. Sample wells 120 are each in fluid communication with a branch channel 126 to one of a plurality of main channels 122. Channels 122 further communicate with reservoir 124. Microcard 120 also comprises an area 170 where information about the card may be written or where a sticker containing information about the card or its contents may be affixed. Such information may be in the form of a bar code, written information, or any other form suitable for displaying desired characteristics of the card or the samples contained therein.

Figure 5:
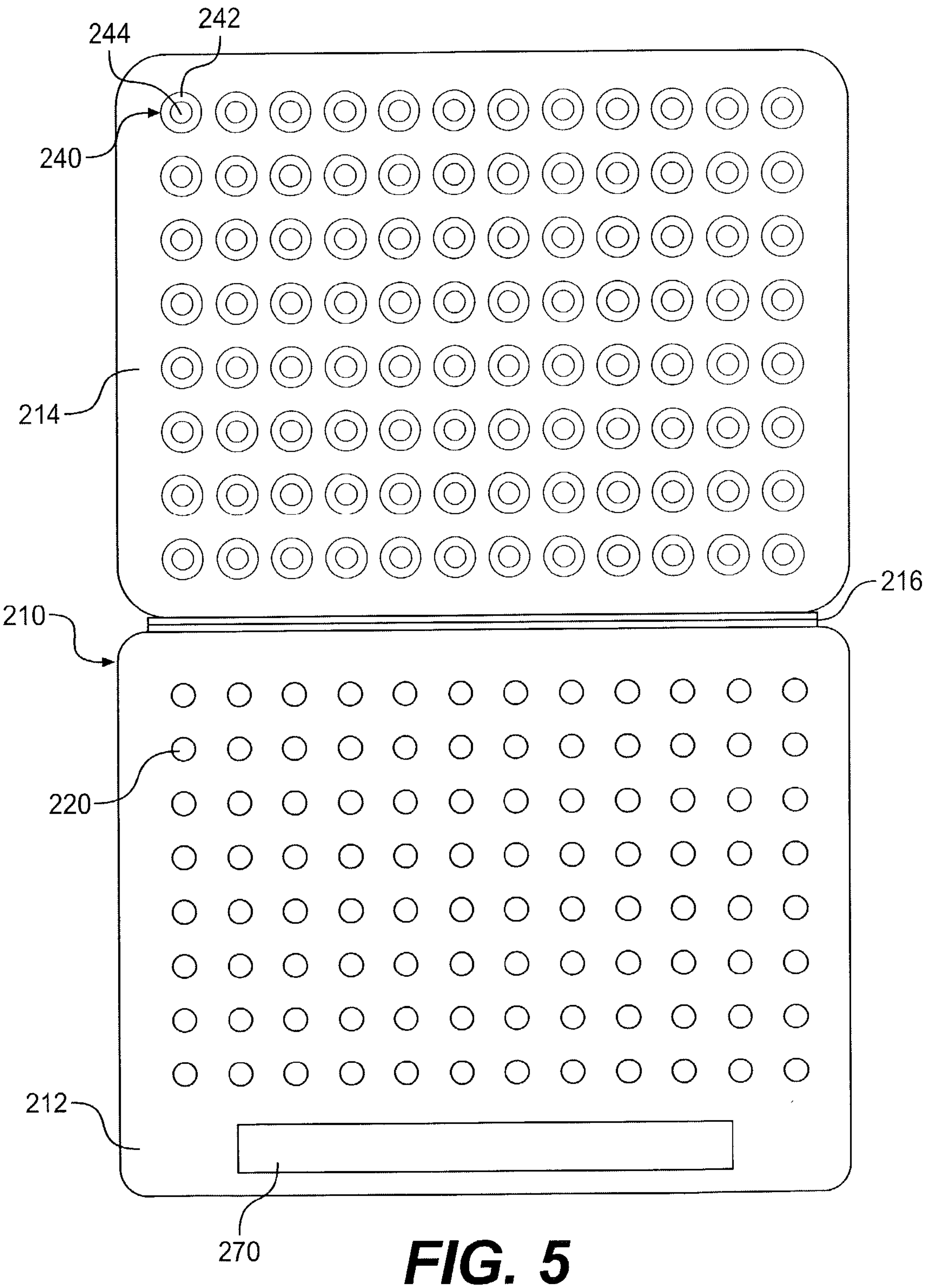
FIG. 5 is a plan view of an alternative embodiment of a microcard in an open position.

According to another embodiment, a microcard 210 is depicted in FIG. 5, which does not include a reservoir or feed channels, but is otherwise substantially similar to microcard 10. Microcard 210 is depicted as having 96 sample wells 220, but any number of sample wells may be provided. Microcard 210 also comprises a first plate 212 and a second plate 214 connected via a hinge 216. Plate 214 includes closure elements 240 comprising a flexible annular rim 242 surrounding a cap 244, which functions in a similar fashion to the closure element described above with reference to FIGS. 1–3. Microcard 210 may be used in a PCR environment whereby a user may desire to fill each sample well 220 separately with each of the reagent and the sample, or any other material desired to be tested. Microcard 210 may be suitable to have completely different reaction materials in one or more of sample wells 220, as desired by a user, or it may be used in a situation where fill equipment such as a vacuum or centrifugal fill is not available. Test fluids may be introduced using a pipette, by hand or automatically, as well as by any other means suitable for filling a microcard sample well.

Figure 6A:
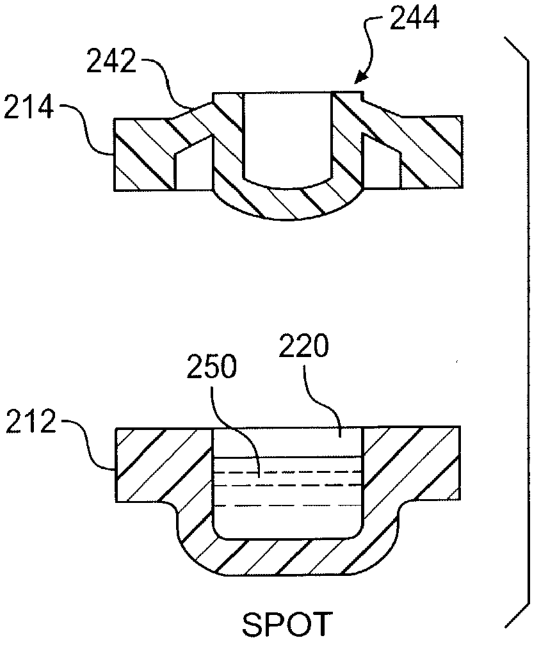
FIGS. 6A–6C are partial section views of a sample well of the microcard of FIG. 5 showing a progression of steps to fill and substantially seal the sample wells.
Figure 6B:
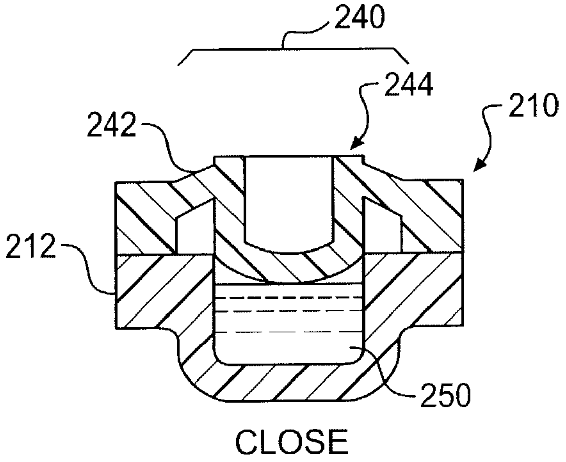
Figure 6C:
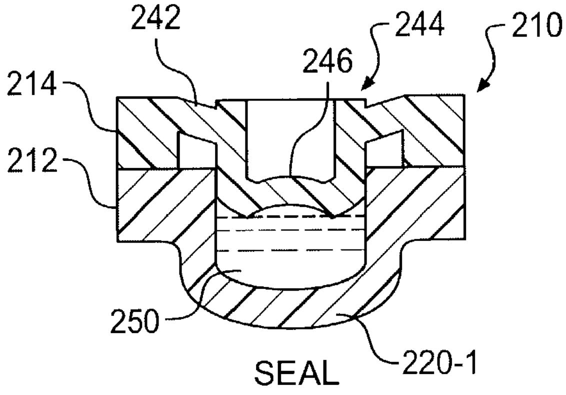

Once filled, microcard 210 may be closed in a similar fashion as described above and as depicted in FIGS. 6A–6C, which show a partial section view of a sample well 220. As seen in FIG. 6A, sample well 220 has been filled or spotted with a desired sample 250 via, for example, pipetting. In this embodiment, sample 250 may comprise both the reagent and the sample, in addition, with this example, spotting may refer to the filling of either one or both of the reagent and the sample. Plate 214 is then positioned over plate 212 to a closed position as depicted in FIG. 6B and in a similar manner as described above in the embodiment of FIGS. 1–3. Because each well 220 is completely isolated within plate 212 a membrane may not be necessary to assist in isolating the various samples. Even though not required, it may be desirable, however, to include a membrane (not shown in FIGS. 6A–6C) similar to membrane 30 (see FIGS. 3A–3D) to assist in maintaining plates 212 and 214 in a closed relationship. Once closed, cap 244 may then be compressed to substantially seal sample well 220 in a similar fashion as described herein with flexible portions 220-1 and 246 bulging to compensate for displaced sample fluid as seen in FIG. 6C.

Figure 7:
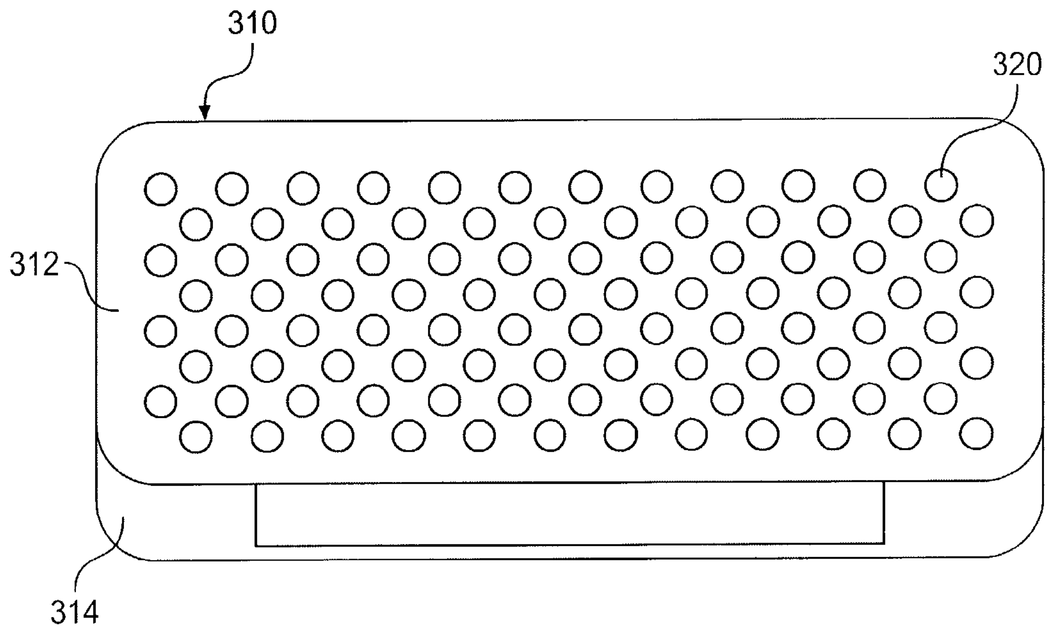
FIG. 7 is a plan view of an alternative embodiment of a microcard.

According to another embodiment similar to microcard 210 depicted in FIG. 5, a closed microcard 310 is shown in FIG. 7 having a first plate 312 and a second plate 314 and 96 sample wells 320. Because the feed channels are not necessary in such a microcard, sample wells 320 may be offset and moved closer together to allow for a smaller overall microcard size and/or to allow for a higher sample well density within a microcard identical in size to microcard 210. In other words, the sample wells in the FIG. 7 embodiment are not positioned in a matrix, unlike the sample wells in the microcards shown in FIGS. 1–6.

Figure 8:
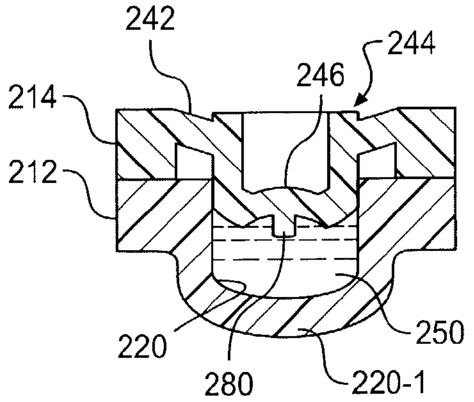
FIG. 8 is a partial section view of a sample well of an alternative embodiment of a microcard having a light pipe.

In another exemplary embodiment, FIG. 8 depicts a sample well 220 having an additional feature of a light pipe 280. Although cap 244 is configured to be immersed within sample 250 to provide the benefit of minimizing the disadvantages of condensation within the well, light pipe 280 may be formed on or as part of flexible portion 246. Light pipe 280 is designed to further extend within sample well 220 to further ensure that a portion of cap 244 is sufficiently immersed within the sample 250. Light pipe 280 may be a cylindrical protrusion of polypropylene, or any other size or shape suitable for the desired radiation transmission characteristics desired with PCR testing. Light pipe 280 may also incorporate optics that may assist in focusing or directing radiation into and out of sample well 220. Flexible annular rim 242 surrounds cap 244, and functions in a manner similar to that described for FIGS. 5–6.

Although microcards 10, 110, 210, and 310 have been described above in relation to a card that has a first member and a second member movable with respect to one another, the present teachings could also apply to a card whereby the first and second members are fixed relative to one another. Such a card could be pre-spotted, as is done with conventional cards, but would contain a plurality of closure elements to substantially seal the sample wells. Essentially, a card of this configuration, instead of using a foil backing, could have a polypropylene member similar to the second member affixed to the first member and containing the closure elements. In this embodiment, for example, a pre-spotted card could incorporate closure elements, therefore allowing the staking to be replaced with moving closure elements in place to substantially seal the sample wells.

It will be apparent to those skilled in the art that various modifications and variations can be made to the structure and methods described above. Thus, it should be understood that the present teachings are not limited to the examples discussed in the specification. Rather, the present teachings are intended to cover modifications and variations.

What is claimed is:

1. A sample substrate for use in biological testing, comprising:

a first member defining a plurality of sample wells for containing a sample to be tested; and a second member including a plurality of sample well closure elements, each sample well closure element being movable with respect to a remainder of the second member, the second member being movable with respect to the first member from an uncovered position, wherein the plurality of sample wells is uncovered, to a covered position, wherein the plurality of sample wells is substantially covered by the second member, at least one of the plurality of sample well closure elements configured to substantially seal a corresponding sample well when the second member is in the covered position, by moving the at least one of the plurality of closure elements from a first predetermined position to a second predetermined position, and at least one reservoir in fluid communication with the at least one of the plurality of sample wells.

2. The sample substrate of claim 1, wherein the reservoir is in fluid communication with the at least one of the plurality of sample wells via a fluid channel.

3. The sample substrate of claim 2, wherein the sample substrate further comprises a branch fluid channel between the fluid channel and the at least one of the plurality of sample wells.

4. The sample substrate of claim 1, wherein the at least one of the plurality of closure elements permits fluid communication between its corresponding sample well and the reservoir when in the first predetermined position and prevents fluid communication between the reservoir and the sample well when in the second predetermined position.

5. The sample substrate of claim 1, wherein the at least one reservoir is capable of being filled with the sample to be tested when the second member is in the covered position.

6. The sample substrate of claim 1, wherein the at least one reservoir comprises a plurality of reservoirs.

7. The sample substrate of claim 6, wherein each of the plurality of reservoirs is in fluid communication with a separate portion of the plurality of sample wells.

8. A sample substrate for use in biological testing, comprising:

a first member defining at least one sample well; and a second member including means for substantially sealing the at least one sample well, the means for substantially sealing being movable with respect to a remainder of the second member from a first predetermined position to a second predetermined position so that at least a portion of the means for substantially sealing lies within the sample well, wherein the means for substantially sealing comprises a movable cap surrounded by a flexible annular rim, the flexible annular rim configured to allow the movable cap to move with respect to the sample well and substantially seal the sample well.

9. The sample substrate of claim 8, wherein the movable cap includes a cylindrical portion configured to engage an inner surface of its corresponding sample well.

10. A sample substrate for use in biological testing, comprising:

a first member defining a plurality of sample wells for containing sample to be tested; and a second member including a plurality of sample well closure elements and a surface connecting the sample well closure elements, each sample well closure element including:

a cap with a projecting member dimensioned to fit into a corresponding sample well; and a flexible annular hinge member connecting the cap and the surface of the second member, the flexible annular hinge member configured to snap between a first discrete position in which the cap substantially covers the corresponding sample well, and a second discrete position in which the cap substantially seals the corresponding sample well.

11. The sample substrate of claim 10, wherein the flexible annular hinge member is initially flexed to the first discrete position, and then snaps to the second discrete position upon a predetermined force being imparted on the cap.

12. The sample substrate of claim 10, wherein the projecting member is cylindrical and the corresponding sample well is cylindrical.

13. The sample substrate of claim 10, wherein the first member further comprises at least one reservoir in fluid communication with at least one of the plurality of sample wells.

14. The sample substrate of claim 13, wherein the first member further comprises a fluid channel so that the reservoir is in fluid communication with the at least one of the plurality of sample wells when the cap is in the first discrete position.

15. The sample substrate of claim 14, wherein the at least one of the plurality of closure elements permits fluid communication between its corresponding sample well and the reservoir when the cap is in the first discrete position and prevents fluid communication between the reservoir and the sample well when the cap is in the second discrete position.

16. The sample substrate of claim 15, wherein in the second discrete position, the bottom portion of the cap blocks the fluid channel from communicating with the at least one of the plurality of sample wells.

17. A sample substrate for use in biological testing, comprising:

a first plate-like member defining an array of sample wells for containing sample to be tested; and a second plate-like member including an array of sample well closure elements and a surface connecting the sample well closure elements, the sample well closure elements being positioned to correspond with the array of sample wells, each sample well closure element including:

a cap with a cylindrical member dimensioned to fit into a corresponding sample well, and a bottom portion; and a flexible annular hinge member connecting the cap and the surface of the second plate-like member, the flexible annular hinge member including an over-center hinge so that the hinge member snaps between a first discrete position in which the cap is spaced from the sample well, and a second discrete position in which the bottom portion of the cap is positioned within the sample well to substantially seal the corresponding sample well.

* * * * *